United States Patent [19]

Nakamura et al.

[11] Patent Number: 4,889,833

[45] Date of Patent: Dec. 26, 1989

[54] GRANULAR INORGANIC MOLDINGS AND A PROCESS FOR PRODUCTION THEREOF

[75] Inventors: Seishiro Nakamura, Kurashiki; Katutoshi Oukami, Soja; Masayuki Asada, Kurashiki, all of Japan

[73] Assignee: Kuraray Co., Ltd., Kurashiki, Japan

[21] Appl. No.: 103,492

[22] Filed: Oct. 1, 1987

[30] Foreign Application Priority Data

Oct. 6, 1986 [JP] Japan .................................. 61-238947

[51] Int. Cl.$^4$ .............................................. C04B 35/00
[52] U.S. Cl. .......................................... 501/1; 264/15; 264/41; 264/56; 264/57
[58] Field of Search ...................... 501/1, 123; 264/44, 264/15, 41, 56, 59; 623/16, 16 C, 16 D

[56] References Cited

U.S. PATENT DOCUMENTS

| | | | |
|---|---|---|---|
| 4,222,128 | 9/1980 | Tomonaga et al. | 501/1 |
| 4,330,514 | 5/1982 | Nagai et al. | 623/16 |
| 4,477,604 | 10/1984 | Oechsle, III | 623/16 |
| 4,497,075 | 2/1985 | Niwa et al. | 623/16 |
| 4,542,539 | 9/1985 | Rowe, Jr. et al. | 623/16 |
| 4,629,464 | 12/1986 | Takata et al. | 623/16 |
| 4,639,283 | 1/1987 | Nakamura | 156/89 |
| 4,645,503 | 2/1987 | Lin et al. | 623/16 |
| 4,654,314 | 3/1987 | Takagi et al. | 623/16 |
| 4,664,858 | 5/1987 | Kido et al. | 264/44 |
| 4,693,986 | 9/1987 | Vit et al. | 501/1 |

FOREIGN PATENT DOCUMENTS

| | | | |
|---|---|---|---|
| 87/07495 | 12/1987 | Int'l Pat. Institute | 623/16 |
| 1228450 | 4/1971 | United Kingdom | 264/15 |

*Primary Examiner*—Olik Chaudhuri
*Assistant Examiner*—Andrew Griffis
*Attorney, Agent, or Firm*—Burns, Doane, Swecker & Mathis

[57] ABSTRACT

Inorganic granules are characterized in that when the maximum extent of a granule is termed D and the dimension perpendicular to the maximum extent has a maximum extent termed A, A/D is 0.5 to 0.9; and in at least 80% of the granules, the position of A crossing with D is within 0.3D on either side of the center of D. Such granules can be obtained in a high yield by introducing inorganic powders capable of calcination into an organic porous body having a 3-dimensional net-like structure and subjecting the porous body to isotropic pressing thereby to form inorganic granules in pores of the porous body. The organic porous body is then burned off and at the same time, the inorganic granules are calcined. The inorganic granules are useful as bone fillers and the like.

5 Claims, 2 Drawing Sheets

1000 μm

Granule A type

Granule B type

Granule A type (crossing point of A and D is within 0.3D) --- X pieces

Granule B type (crossing point of A and D is out of 0.3D) --- Y pieces

X/X+Y > 80%

GRANULAR INORGANIC MOLDINGS AND A PROCESS FOR PRODUCTION THEREOF

BACKGROUND OF THE INVENTION

1. Field of the Invention

The present invention relates to inorganic granules comprising inorganic compounds such as calcium phosphates, metal oxides and mixtures thereof or the like, and to a process for production thereof. The inorganic granules are useful as fillers for bony defects or as carriers for immobilized enzymes or catalysts.

2. Description of the Prior Art

Calcium phosphate granules, which are representative of inorganic granules, promote formation of new bone and integrate with the living bone tissue. Their use as bone fillers has thus been attempted.

As processes for production of calcium phosphate granules, there are known (a) a process which comprises grinding the dry product of calcium phosphates prepared by the wet process into granules, as is or after precalcination, and then sifting the granules (Journal of American Chemical Society, 89, 5535 (1967), Published Unexamined Japanese Patent Application No. 20558/86, etc.), (b) a process which comprises repeatedly stirring calcium phosphate powders with a high speed stirring machine in the presence of alcohol as a medium while moisturizing, to form granules of a desired size (Published Unexamined Japanese Patent Application No. 45748/86, etc. The calcium phosphate granules obtained by the processes as described above have uneven shapes in respective granules so that, in the case of using them as bone fillers, problems often occur in that the filling state is not uniform and they do not exhibit stable efficiency. In addition, the calcium phosphate granules obtained by the process (a) described above have edges that agitate bone cells and there is thus a fear of causing necrosis of the cells, in the case of filling them in a bony defect. Further, the calcium phosphate granules obtained by the process (b) described above give high density granules only with difficulty, even after calcination, and there is also a problem that mechanical strength thereof is poor for their use as bone fillers.

Furthermore, if granules of a desired size are sought to be made by these processes, there is a problem that yield is poor due to production of undesired powders in large quantities in either of the processes (a) and (b).

SUMMARY OF THE INVENTION

Accordingly, an object of the present invention is to provide inorganic granules, especially calcium phosphate granules, having a uniform shape and which are useful as bone fillers.

Another object of the present invention is to prepare such inorganic granules in a high yield.

These objects can be achieved by inorganic granules characterized in that when the maximum extent of a granule is termed D and the dimension perpendicular to the maximum extent has a maximum extent termed A, A/D is 0.5 to 0.9; and in at least 80% of the granules, the position of A crossing with D is within 0.3D on either side of the center of D. Such inorganic granules can be obtained in a high yield by introducing inorganic powders capable of calcination into an organic porous body having a 3-dimensional net-like structure, subjecting the porous body to isotropic pressing thereby to form granular inorganic moldings in pores in the porous body, burning off the organic porous body and at the same time, calcining the granular inorganic moldings.

DETAILED DESCRIPTION OF THE INVENTION

Figure 1:
FIG. 1 is an electron microscopic photograph showing an example of calcium phosphate granules obtained by the present invention.
Figure 2:
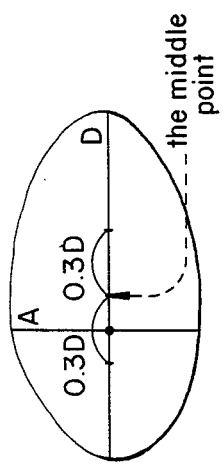
FIG. 2 is a schematic representation of granules within and without the scope of the present invention, illustrating the relation between the parameters A and D described above.
Figure 2:
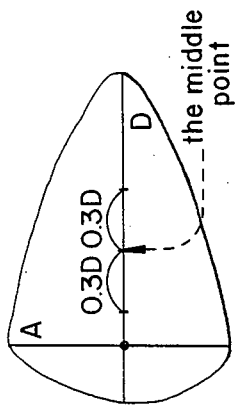

As inorganic components constituting the inorganic granules of the present invention, mention may be made of those mainly composed of calcium phosphates and those mainly composed of metal oxides as described below.

(1) Calcium phosphates such as tricalcium phosphate, hydroxyl apatite, tetracalcium phosphate, oxy apatite, calcium pyrophosphate, fluoro apatite, compounds in which a part of hydroxyl apatite is substituted with fluorine ions, mixtures thereof, etc.; tricalcium phosphate, hydroxyl apatite and mixtures thereof are especially preferred. Other inorganic components, for example, metal oxides such as alumina and zirconia, etc. may be mixed with calcium phosphate in a small quantity (about 20% or less by weight based on calcium phosphate).

(2) Metal oxides such as alumina, zirconia, titania, silica, silica alumina or mixtures thereof, etc.

The inorganic granules of the present invention are characterized in that when the maximum extent of a granule is termed D and the dimension perpendicular to the maximum extent has a maximum extent termed A, A/D is 0.5 to 0.9; and in at least 80% of the granules, the position of A crossing with D is within 0.3D on either side of the center of D. Therefore, the shape of each granule constituting a group of granules is uniform so that stable efficiency can always be obtained. Measurement of the shape of the granules can be performed by electron miroscopic photography.

With A/D less than 0.5, the granules are easily powdered owing to sharp edged shapes. On the other hand, with A/D more than 0.9, it is difficult to fill densely with the granules, and the filled granules are movable. Further, with less than 80% of the above-mentioned granules, it is difficult to obtain a uniform filling state.

As will be described below, the inorganic granules of the present invention are prepared by inserting inorganic powders capable of calcination into an organic porous body having a 3-dimensional net-like structure, performing isotropic pressing thereby to form inorganic granules in pores of the porous body and then burning off the organic porous body. Therefore, the inorganic granules of the present invention are characterized in that each granule is not only uniform in its shape but also free from edges. The inorganic granules of the present invention are also characterized in that they have a high density depending upon pressing pressure and calcination temperature, they are polyhedral depending upon the pore shape of the organic porous body used, or linear grooves may be observed on the surface of granules.

The inorganic granules of the present invention can be obtained by subjecting to isotropic pressing powders of inorganic compounds mainly composed of calcium phosphates or metal oxides as described above in the pores of an organic porous body. As the raw powders used in the present invention, those having a size of 0.5 to 500μ are generally preferred, with particular preference of 1 to 200μ, which size is appropriately chosen depending upon the size of granules to be obtained. It is also desired that the content of water in the powders be 5% or less.

An example of the organic porous body having a 3-dimensional net-like structure used in the present invention includes a polyurethane foam. The size and shape of the polyurethane foam can be controlled depending upon the conditions of its preparation. Accordingly, the size and shape of the inorganic granules can be varied by selecting the cell size and shape of the polyurethane foam. By the use of such foam, inorganic granules up to a maximum diameter of 0.1 to 2 mm, which is a size of ordinary granules, can be prepared. The porous body having a 3-dimensional net-like structure is not limited to polyurethane foam, but can be any organic porous body having a cell of size and shape similar to the polyurethane foam; for example, those made of polyethylene or polystyrene can also be used. It is preferred that the porosity be as large as possible; with a porosity of 80% or more, a desired shape can be obtained in a good yield. In order to prepare a group of granules having a uniform shape in a good yield, it is required that the diameter distribution of pores be uniform. However, commercially available porous bodies having a 3-dimensional net-like structure have uniformity sufficient to prepare the inorganic granules of the present invention.

The inorganic powders are packed in the organic porous body described above followed by press fabrication. As the press fabrication, preferred is isotropic pressure molding, inter alia, cold isostatic press fabrication. In the cold isostatic press fabrication, the organic porous body is inserted in close contact with a rubber matrix (usually made of rubber but may be made of any elastic body other than rubber), in which the inorganic powders are packed.

The rubber matrix packed with the inorganic powder-filled porous body is pressed by cold isostatic press fabrication (also called rubber press method), in which the pressing pressure is generally 300 to 6000 kg/cm$^2$. With a pressure of 300 kg/cm$^2$ or less, it is difficult to obtain granules having a sufficient strength. Further, with a pressure of 6000 kg/cm$^2$ or more, partial cracking occurs in the inorganic granules when subsequently calcined. By performing the press fabrication described above, the inorganic powders become granular in the pores of porous body.

After the press fabrication is performed, the organic porous body is calcined out, whereby the inorganic granules can be taken out. At the same time, the inorganic granules are calcined to become high in density and to increase their mechanical strength.

In the case of calcium phosphate granules, it is preferred that heating be conducted at 500° to 1400° C., more preferably 600° to 1300° C. At lower than 500° C., carbon from the organic porous body remains in the calcium phosphate calcination products and such is not preferred. At higher than 1400° C., cracking tends to occur in the calcium phosphate calcination products obtained. When porous granular calcium phosphate calcination products are required, it is desired to calcine at temperatures of 900° C. or less; when dense granules (relative density of 90% or more) are required, it is desired to calcine at temperatures of 900° C. or more.

Further, in the case of the metal oxide granules, it is preferred that the heating be carried out at 500° to 2000° C. At lower than 500° C., carbon from the organic porous body remains in the metal oxide calcination products and such is not preferred. At higher than 2000° C., cracking tends to occur in oxide calcination products obtained. When porous granular metal oxide calcination products are required, it is desired to calcine at temperatures of 1300° C. or less; when dense granules (relative density of 90% or more) are required, it is desired to calcine at temperatures of 1300° C. or more, for example, in the case of alumina.

As above, inorganic granules having a uniform shape can be obtained in a high yield by inserting the inorganic powders into the organic porous body having a 3-dimensional net-like structure, performing press fabrication and then calcining the organic porous body. The granules obtained by the process of the present invention not only have a uniform shape but also are free from edges. Further, depending upon press conditions or calcination conditions, the granules have a high density of 90% or higher in relative density and high mechanical strength. Furthermore, the granules have a polyhedral shape depending upon the shape of pores of the organic porous body used and it is also a characteristic that linear grooves are observed on the surface of a part of the granules. In addition, the process of the present invention is advantageous in that the granules can be obtained in a high yield but its operation is simple.

Hereafter the present invention will be described in more detail with reference to the examples below, but is not deemed to be limited thereto.

EXAMPLE 1

Calcium phosphate powders (Ca/P atomic ratio=1.67; grain diameter of the powders, 5-20μ; specific surface area, 59 m$^2$/g) manufactured by Taihei Chemical Industrial Co., Ltd. were packed in 10 pieces of polyurethane foam "Everlightscott Filter" (HR-13; cell number, 11-16 cells/25 mm; porosity, 97%) manufactured by Bridgestone Corporation, which was then inserted in a rubber form (inner volume of 2 cm×5 cm×5 cm) and pressed with a rubber press under a pressure of 2000 kg/cm$^2$. After the rubber pressing, the polyurethane foam containing the calcium phosphate powders (the calcium phosphate powders were in a granular form in pores of the foam) was put in an electric furnace and calcined at 500° C. for 3 hours. After elevating the temperature to 1200° C., calcination was performed for 2 hours. The thus obtained granular calcium phosphate calcination product was sieved to give 326 g of ellipsoidal calcium phosphate calcination product of 12 to 28 mesh (sieve opening; 580 to 1400μ). The yield of the granular calcium phosphate calcination product obtained per 340 g of the calcium phosphate powders packed in 10 pieces of the polyurethane foam was 96%. Further, relative density of the granular calcium phosphate calcination product was 98.3% as a result of measurement by the nitrogen adsorption method, and product of high density was obtained.

By electron microscopic photography (magnification: 26), 50 pieces of the granular calcium phosphate calcination product obtained were observed (10 pictures were taken . . . 4 to 6 granules per picture) and the parameters D and A were measured. As a result, A/D was 0.76 and the number of granules where the position of A crossing with D was within 0.3D on either side of the center of D was 92% of the total number of granules.

The granules were packed in a cavity formed on the jaw bone of a dog, which was sacrificed 30 days thereafter to prepare a specimen. As a result of observation of tissue in the specimen, spaces between the calcium phosphate granules were completely filled up with new bone.

EXAMPLE 2

Granular hydroxyl apatite calcination product was prepared in a manner similar to Example 1 except that hydroxyl apatite HCA-100s (Ca/P atomic ratio=1.67; grain diameter of the powders, 10 to 100μ; specific surface area, 6 m$^2$/g) manufactured by Mitsui Toatsu Chemicals, Inc. was used instead of calcium phosphate powders manufactured by Taihei Chemical Industrial Co., Ltd. The obtained ellipsoidal hydroxyl apatite calcination product of 12 to 28 mesh (sieve opening: 580 to 1400μ) was 333 g based on 362 g of the hydroxyl apatite powders packed in the polyurethane foam and the yield was 92%. Further, the relative density of the hydroxyl apatite calcination product was 94.5%.

In a manner similar to Example 1, the parameters D and A of the hydroxyl apatite calcination product were measured. As a result, A/D was 0.72 and the number of granules where the position of A crossing with D was within 0.3D on either side of the center of D was 80% of the total number of granules.

EXAMPLE 3

In 7.1 l. of distilled water there was dissolved 2500 g of commercially available calcium nitrate [Ca(No$_3$)$_2$.4-H$_2$O], and 7.9 l. of 28% ammonia water was slowly added to the resultant solution. The thus obtained solution was then diluted with 3 1. l. of distilled water. Separately therefrom, 840 g of commercially available ammonium hydrogen-phosphate [NH$_4$)$_2$HPO$_4$] was dissolved in 10 l. of distilled water. 4.8 l. of 28% ammonia water and 10 l. of distilled water were then added to this solution. While keeping the former calcium nitrate aqueous solution at 20° C., the latter ammonium hydrogenphosphate aqueous solution (20° C.) was added dropwise thereto with stirring to effect reaction therebetween. After completion of the dropwise addition, the mixture described above was heated to 80° C. and maintained for 20 minutes under reflux, while continuing stirring. After cooling, the reaction mixture was allowed to settle for 2 days. Subsequently, the solution was dehydrated (2000 g) with a centrifugal dehydrator equipped with a polypropylene-made filter cloth (1000 mesh) and washed with distilled water until the system showed no alkaline property. The thus obtained calcium phosphate filtered cake was dried and then ground into powders in a mortar. The powders were passed through a sieve of 140 mesh to give 920 g of calcium phosphate powders. The calcium phosphate powders were packed in 18 pieces of polyurethane foam "Everlightscott Filter" (HR-20; cell number, 17-25 cells/25 mm; porosity, 97%) manufactured by Bridgestone Corporation, which were then each inserted in a respective rubber form as in Example 1. Three pieces each in a group were pressed with a rubber press under 6 levels of pressure as shown in Table 1. They were put in an electric furnace and calcined for 2 hours at 1100° C., after elevating the temperature to 1100° C.

The thus obtained ellipsoidal granular calcium phosphate calcination products were sifted to give the ellipsoidal calcium phosphate calcination product of 20 to 42 mesh (sieve opening 400 to 830μ) in yields shown in Table 1. X-ray diffraction patterns of the calcium phosphate calcination products were identical with that of hydroxyl apatite.

TABLE 1

| Pressure of Rubber Press (kg) | Granular Calcium Phosphate Calcination Product having a Size of 20 to 42 Mesh | | Relative Density Note 2 | E (%) | |
|---|---|---|---|---|---|
| | Yield (%) (g) Note 1 | | | % | A/D Note 3 |
| 250 | 74 | 72 | 86 | 0.71 | 83 |
| 350 | 91 | 88 | 93 | 0.70 | 83 |
| 1000 | 95 | 92 | 97 | 0.68 | 90 |
| 2000 | 98 | 95 | >99 | 0.67 | 91 |
| 5000 | 91 | 88 | >99 | 0.65 | 91 |
| 5500 | 80 | 78 | >99 | 0.65 | 93 |

Note 1 Total amounts of 3 pieces of polyurethane foam.
Note 2 103 g of calcium phosphate powders packed in 3 pieces of polyurethane foam.
Note 4 E indicates a percentage of the number of obtained granules where the position of A crossing with D was within 0.3D on either side of the center of D.

COMPARATIVE EXAMPLE 1

Calcium phosphate filter cake was prepared in a manner similar to Example 3. After drying, the calcium phosphate was broken by a hammer mill. The obtained broken calcium phosphate was calcined at the same temperatures as in Example 3.

The thus broken calcium phosphate calcination product was sieved to give 420 g of granular calcium phosphate calcination product of 20 to 42 mesh (sieve opening: 400 to 830μ). The yield of the obtained granular calcium phosphate calcination product was 40% based on the theoretical amount 1060 g of gelatin-like calcium phosphate precipitates. The relative density of the calcium phosphate calcination product was 99.2%, but most of the granules had sharp edges. In a manner similar to Example 1, the parameters D and A of the granular calcium phosphate calcination product were measured. As a result, A/D was 0.52 and the number of granules where the position of A crossing with D was within 0.3D on either side of the center of D was 52% of the total number of granules.

The granules were embedded in the jaw bone of a dog in a manner similar to Example 1, and the tissue was thereafter observed. As a result, a large number of fibrous connective tissues were noted in the spaces of the calcium phosphate calcination product together with new bone.

COMPARATIVE EXAMPLE 2

The calcium phosphate precipitates obtained in Example 3 by dehydrating with a centrifugal dehydrator and washing were dried at the same temperature as in Example 1, as they were in the shape of the filter cake. After drying, the calcium phosphate filter cake was put in a mortar having a diameter of 30 cm and ground so as to pass at least 95% of the dry calcium phosphate through a sieve of 8 mesh (sieve opening: 2.0 mm) and to give a maximum amount of dry calcium phosphate between 16 and 32 mesh (sieve opening: 500 to 100 μ). The granular dry calcium phosphate obtained by grinding was put in an electric furnace and calcined at the same temperature as in Example 1. The thus obtained calcium phosphate calcination product was again sieved to give 350 g of the calcium phosphate granules of 20 to 42 mesh (sieve opening: 400 to 830μ) having the same size as in Example 1. The yield of the obtained granular calcium phosphate calcination product was 33% based on the theoretical amount 1060 g of gelatin-like calcium phosphate precipitates. The remaining calcium phosphate calcination product mostly passed through 60 mesh (sieve opening: 250μ). The relative density of the calcium phosphate calcination product was 99.3% but most of the granules had sharp edges.

EXAMPLE 4

Granular ellipsoidal calcium phosphate calcination product was prepared in a manner similar to Example 1 except that β-tricalcium phosphate powders (Ca/P atomic ratio=1.50; specific surface area, 1 m$^2$/g) manufactured by Taihei Chemical Industrial Co., Ltd. were used. The obtained ellipsoidal calcium phosphate calcination product of 12 to 28 mesh was 319 g based on 355 g of β-tricalcium phosphate packed in the polyurethane foam and the yield was 90%. Further, the relative density of the calcium phosphate calcination product was 90.3%.

In a manner similar to Example 1, the parameters D and A were measurd. As a result, A/D was 0.72 and the number of granules where the position of A crossing with D was within 0.3D on either side of the center of D was 86% of the total number of granules.

EXAMPLE 5

Ten pieces of pressed polyurethane foam packed with the hydroxyl apatite powders were prepared in a manner similar to Example 1 except that hydroxyl apatite AN powders (Ca/P=1.67; specific surface area, 36 m$^2$/g; grain diameter of the powders, 10 to 30μ) manufactured by Central Glass Co., Ltd. were used. They were put in an electric furnace and calcined at 600° C. for 3 hours. The thus obtained ellipsoidal hydroxyl apatite calcination product was sieved to give 295 g of the ellipsoidal hydroxyl apatite calcination product of 12 to 28 mesh. The yield of the granular calcium phosphate calcination product was 89% based on 332 g of the hydroxyl apatite powders packed in the 10 pieces of polyurethane foam. Further, the relative density of the calcium phosphate calcination product was 52%, and the hydroxyl apatite calcination product was a porous body having a pore diameter of 70 to 250 Å in which the pore volume was 83% based on the total pore volume.

In a manner similar to Example 1, the parameters D and A were measured. As a result, A/D was 0.75 and the number of granules where the position of A crossing D was within 0.3D on either side of the center of D was 82% based on the total number of granules.

EXAMPLE 6

Partially stabilized zirconia powders (specific surface area, 6 m$^2$/g; Y$_2$O$_3$, 3 mol %) manufactured by Daiichi Kigenso Chemical Industry Co., Ltd. were packed in 10 pieces of polyurethane foam "Everlightscott Filter" (HR-13; cell number, 11-16 cells/25 mm; porosity, 97%) manufactured by Bridgestone Corporation, which were then each inserted in a respective rubber form (inner volume of 2 cm×5 cm×5 cm), and pressed with a rubber press under a pressure of 2000 kg/cm$^2$. After the rubber pressing, the polyurethane foam containing the zirconia powders (the zirconia powders were in granular form in pores of the foam) was put in an electric furnace and calcined at 500° C. for 2 to 3 hours. After elevating the temperature to 1500° C., calcination was performed for 2 hours. The thus obtained granular zirconia calcination product was sieved to give 570 g of the ellipsoidal zirconia calcination product of 8 to 28 mesh (sieve opening: 580 to 2400). The yield of the granular zirconia calcination product obtained was 95% based on 602 g of the zirconia powders packed in 10 pieces of the polyurethane foam. Further, the relative density of the granular zirconia calcination product was 99% as a result of measurement by the nitrogen adsorption method, and a product of high density was obtained.

In a manner similar to Example 1, the parameters D and A of the granular zirconia calcination product were measured. As a result, A/D was 0.68 and the number of granules where the position of A crossing with D was within 0.3D on either side of the center of D was 82% of the total number of granules.

EXAMPLE 7

Granular alumina calcination product was prepared in a manner similar to Example 1 except that alumina powders (specific surface area, 145 m$^2$/g) manufactured by Catalysts & Chemicals Industries Co., Ltd. were used and the calcination was conducted at an electric furnace temperature of 1800° C. The obtained ellipsoidal alumina calcination product of 12 to 28 mesh (580 to 1400μ) was 279 g based on 310 g of the alumina powders packed in the polyurethane foam and the yield was 90%. Further, the relative density of the alumina calcination product was 96%.

In a manner similar to Example 1, the parameters D and A of the alumina calcination product were measured. As a result, A/D was 0.78 and the number of granules where the position of A crossing with D was within 0.3D on either side of the center of D was 91% of the total number of granules.

EXAMPLE 8

Granular alumina calcination product was prepared in a manner similar to Example 7 except that the calcination was conducted at an electric furnace temperature of 1200° C. The yield of obtained ellipsoidal alumina calcination product of 8 to 24 mesh (sieve opening: 720 to 2400μ) ws 87%. Further, the relative density of the alumina calcination product was a porous body in which the volume of pores having a pore diameter of 1200 to 1600 Å was 81% of the total pore volume.

In a manner similar to Example 1, the parameters D and A of the alumina calcination product were measured. As a result, A/D was 0.82 and the number of granules where the position of A crossing with D was within 0.3D on either side of the center of D was 84% of the total number of granules.

EXAMPLE 9

Ellipsoidal calcium phosphate-zirconia mixture calcination product was prepared in a manner similar to Example 1 except that a mixture of hydroxyl apatite AN manufactured by Central Glass Co., Ltd. and partially stabilized zirconia powders manufactured by Daiichi Kigenso Chemical Industry Co., Ltd. (weight ratio 10:1) was used. The obtained ellipsoidal calcium phosphate-partially stabilized zirconia mixture calcination product of 12 to 28 mesh was 285 g based on 320 g of the mixture of powders packed in the polyurethane foam, and the yield was 89%. Further, the relative density of the calcium phosphate-zirconia mixture calcination product was 93%.

In a manner similar to Example 1, the parameters D and A of the calcium phosphate-zirconia mixture calcination product were measured. As a result, A/D was 0.70 and the number of granules where the position of A crossing with D was within 0.3D on either side of the center of D was 86% of the total number of granules.

What is claimed is:

1. A process for producing inorganic granules, comprising burning a porous organic body having inorganic powder compacted therein, thereby to produce calcined inorganic granules having a shape determined by said porous organic body.

2. The process according to claim 1, wherein said inorganic powder is compacted in said porous organic body by cold isostatic pressing.

3. The process according to claim 1, wherein said calcining step is performed at a temperature of at least about 500° C.

4. The process according to claim 1, wherein said porous organic body is a foamed polymeric substance.

5. The process according to claim 4, wherein said foamed polymeric substance is a polyurethane foam.

* * * * *